United States Patent [19]

Levy et al.

[11] Patent Number: 4,920,143

[45] Date of Patent: Apr. 24, 1990

[54] HYDRO-MONOBENZOPORPHYRIN WAVELENGTH-SPECIFIC CYTOTOXIC AGENTS

[75] Inventors: Julia G. Levy; David Dolphin, both of Vancouver; Jack K. Chow, Burnaby; Ethan Sternberg, Vancouver, all of Canada

[73] Assignee: University of British Columbia, Vancouver, Canada

[21] Appl. No.: 221,161

[22] Filed: Jul. 19, 1988

Related U.S. Application Data

[63] Continuation-in-part of Ser. No. 41,680, Apr. 23, 1987, which is a continuation-in-part of Ser. No. 5,204, Jan. 20, 1987.

[51] Int. Cl.$^5$ .................... A61K 31/40; C07D 437/22
[52] U.S. Cl. ..................................... 514/410; 540/145
[58] Field of Search .......................... 540/145; 514/410

[56] References Cited

U.S. PATENT DOCUMENTS 2,951,800  9/1960  Sharp ................................ 204/162
4,649,151  3/1987  Dougherty et al. ............... 514/410
4,675,338  6/1987  Bommer et al. .................... 514/410

OTHER PUBLICATIONS

Morgan et al., Chemical Abstracts, vol. 102, (1985), 61981s.
Pangka et al. Chemical Abstracts, vol. 104, (1986), 207015v.
Richter et al., Chemical Abstracts, vol 108, (1988), 146293t.
Diamond et al., Lancet, (1972), 2:1175–1177.
Dougherty et al., Cancer Res., (1978), 38:2628–2635.
Dougherty et al., "The Science of Photo Medicine", (1982), Regan & Parish editors, pp. 625–638.
Dougherty et al., "Cancer: Principles and Practices of Oncology", (1982), DeVita et al., editor, pp. 1836–1844, (A copy is currently not available).
Dougherty et al., "Porphyrin Localization and Treatment of Tumors", (1984), pp. 301–314.
Dougherty et al., CRC Critical Rev. in Oncology/Hematology, (1984) 2:83–116.
Gregorie et al., Ann. Surg., (1968), 167:827–829.
Dougherty et al., "Porphyrin Photosensitization," Kessel et al., editors, (1983), Plenum Press, pp. 3–12.
Mew et al., J. Immunol., (1983), 130:1473–1477.
Mew et al., Cancer Res., (1985), 45:4380–4386.
Weishaupt et al., Cancer Res., (1976), 36:2326–2329.
Morgan et al., (1984), J. Chem. Soc. Chem. Commun., pp. 1047–1948.
Richter et al., (1987), JNCI 79(6):1327–1331.
Pangka et al., (1986), J. Organic Chem. 51:1094–1100.

Primary Examiner—Richard L. Raymond
Attorney, Agent, or Firm—Irell & Manella

[57] ABSTRACT

A group of hydro-monobenzoporphyrins "green porphyrins" (Gp) having absorption maxima in the range of 670–780 nanometers is useful in treating disorders or conditions which are subject to hematoporphyrin derivative (HPD) treatment in the presence of light, or in treating virus, cells and tissues generally to destroy unwanted targets. The use of the Gp of the invention permits the irradiation to use wavelengths other than those absorbed by blood. The Gp of the invention may also be conjugated to ligands specific for receptor or to specific immunoglobulins or fragments thereof to target specific tissues or cells for the radiation treatment. Use of these materials permits lower levels of drug to be used, thus preventing side reactions which might destroy normal tissues.

11 Claims, 4 Drawing Sheets

1.

3.

5.

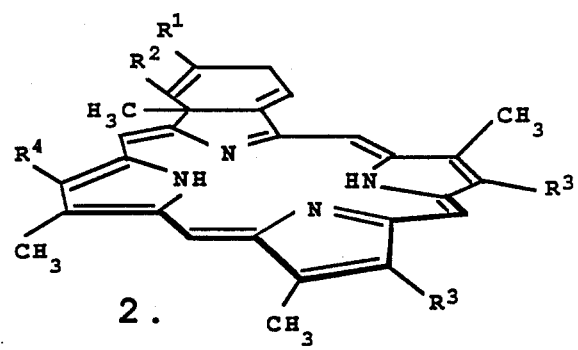
2.
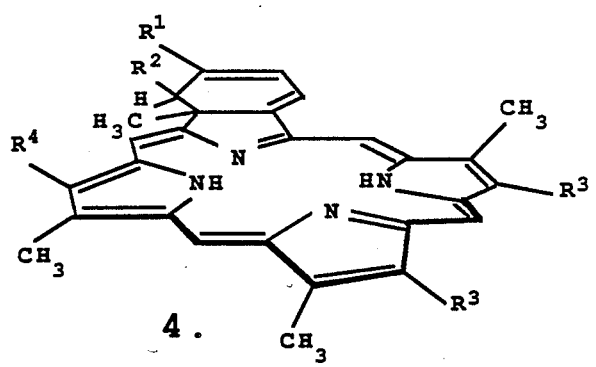
4.
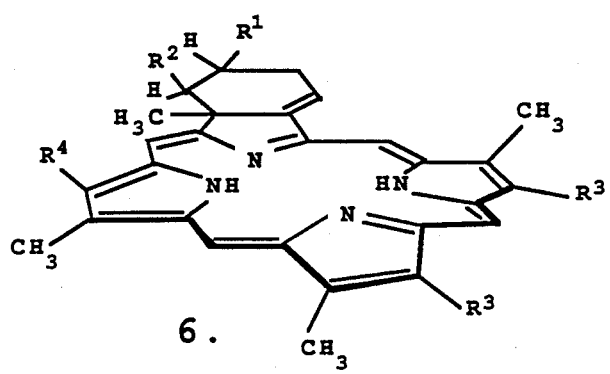
6.
Fig. 1 (con't)

HYDRO-MONOBENZOPORPHYRIN WAVELENGTH-SPECIFIC CYTOTOXIC AGENTS

CROSS-REFERENCE TO RELATED PATENT APPLICATION

This is a continuation-in-part of U.S. Ser. No. 041,680, filed 23 Apr. 1987 which is a continuation-in-part of U.S. Ser. No. 005,204, filed 20 Jan. 1987.

FIELD OF THE INVENTION

The invention relates to the use of light absorbing compounds to mediate the destruction of unwanted cells or tissues or other undesirable materials by irradiation. Specifically, the invention relates to the use of hydro-monobenzoporphyrin derivatives having absorption maxima in the range 670-780 nanometers to mediate the irradiation of materials to be destroyed, and to the use of these compounds conjugated to target-specific ligands, such as receptor-specific ligands, or immunoglobulins or their immunospecific fragments, to focus the effects of the irradiation on particular targets.

BACKGROUND OF THE INVENTION

The use of hematoporphyrin and its acetylated derivative mixture hematoporphyrin derivative (HPD) systemically, combined with irradiation, for the detection and treatment of malignant cells has, by this time, some considerable history. HPD is a mixture of porphyrins including hematoporphyrin itself, hydroxyethyl vinyl deuteroporphyrin, protoporphyrin, and dihematoporphyrin ethers. (See, e.g., "Porphyrin Photosensitization", Kessee, D., et al, eds. (1983) Plenum Press.)

HPD seems "naturally" capable of localizing in malignant cells. When irradiated, it has two properties which make it useful. First, when irradiated with ultraviolet or visible light, it is capable of fluorescence, and thus is useful in diagnostic methods related to detection of malignancy (see, for example, Kessee, et al (supra); Gregory, H.B. Jr., et al, *Ann Surg* (1968) 167:827-829). More pertinent to the present invention is the capacity of HPD, when irradiated with visible light, to exhibit a cytotoxic effect on the cells in which it is localized (see, for example, Diamond, I., et al, *Lancet* (1972) 2:1175-1177; Dougherty, T. J., et al, *Cancer Research* (1978) 38:2628-2635; Dougherty, T. J., et al, "The Science of Photo Medicine" (1982) J. D. Regan & J. A. Parrish eds., pp. 625-638; Dougherty, T. J., et al, "Cancer: Principles and Practice of Oncology" (1982) V.T. DeVita Jr., et al, eds., pp. 1836-1844). Although it has not been definitively established, the effect of HPD in killing cells seems to be due to the formation of singlet oxygen upon irradiation (Weishaupt, K.R., et al, *Cancer Research* (1976) 36:2326-2329). Several mechanisms for this effect have been proposed, and it has recently been shown that the active ingredient in HPD which mediates the cytotoxic effect of visible light irradiation is the mixture of dihematoporphyrin ethers (DHE) (Dougherty, T.J., et al, "Porphyrin Localization and Treatment of Tumors" (1984) pp. 301-314; Dougherty, T. J., *CRC Critical Reviews in Oncoloqy/Hematology* (1984) 2:83-116).

A purified form of the active component(s) of HPD is obtained by adjustment of pH to cause aggregation and recovery of the aggregate, as disclosed in U.S. Pat. No. 4,649,151. The purified form, called DHE in the patent, is marketed under the trademark Photofrin ® II and has been used in a manner completely analogous to HPD.

While the treatment of tumors with HPD relies on the intrinsic ability of HPD to localize in malignant cells, a considerable improvement and refinement in specificity has been achieved by conjugating the hematoporphyrin to tumor-specific antibodies. For example, when hematoporphyrin was coupled to monoclonal antibodies directed to a murine myosarcoma cell line Ml, administration of anti-Ml hematoporphyrin-conjugates to tumor-bearing animals followed by exposure to incandescent light resulted in the suppression of Ml growth (Mew, D., et al, *J Immunol* (1983) 130:1473-1477). In additional work, hematoporphyrin was conjugated to a monoclonal antibody specific to an antigen associated with a human leukemia (CAMAL) and the conjugates were shown to mediate the irradiation-induced killing of leukemic cells specifically, in vitro (Mew, D., et al, *Cancer Research* (1985) 45:4380-4386).

While the conjugation of hematoporphyrin to immunoglobulins specific for targeted cells refines the ability of the hematoporphyrin to home to the desired cells or tissue, this still does not solve another problem ancillary to this general therapeutic approach, namely that the wavelength for irradiation required to activate the hematoporphyrin or HPD, which is in the range of 630 nanometers, is also an energy which is readily absorbed by the porphyrins and other natural chromophores in the blood and other tissues. Therefore, relatively large amounts of the hematoporphyrin or HPD must be administered, often resulting in oversensitization of the patient to light in general. It would be desirable to administer compounds to mediate the effects of irradiation in a lower amount, thus avoiding the problems of hypersensitivity exhibited nonspecifically throughout the subject organism. The activity of certain of these compounds was described in a paper by Richter, A.M., et al, in *J Natl Cancer Inst* (1987) 79:6, mailed to subscribers on 19 Jan. 1988. The invention is directed to the use of such compounds.

DISCLOSURE OF THE INVENTION

The invention provides light absorbing compounds capable of exhibiting light-mediated cytotoxic effects. These compounds may be administered in relatively low dosage due to their capability to absorb radiation whose energy range is outside of that normally absorbed by the components present in high concentration in the blood or other tissues, in particular the porphyrin residues normally associated with hemoglobin and myoglobin. Therefore, by providing these modified porphyrins at lower concentration, the irradiation treatment can be conducted at a wavelength at which the native chromophores do not compete for photons with the active compounds. This results in greater depth of penetration of the light and reduces hypersensitivity of nontarget tissues.

The same advantages accrue in in vitro treatment of colored materials, such as blood samples. These photoactive compounds are modified porphyrins which, by virtue of their derivatization, undergo a shift in absorption maxima so that they appear green rather than red, indicating their absorption of wavelengths in the red-orange range. This collection of derivatives has therefore been nicknamed "green porphyrin" and has been shown to confer sensitivity on target cells at concentrations greater than 10-fold lower than those required for hematoporphyrin (Hp) or HPD. The formulas shown in FIG. 1 represent the green porphyrins of the invention. Also, for convenience, as these are the preferred forms of Gp, an abbreviation of the term hydromonobenzoporphyrin derivative—"BPD"—is generally used to refer to compounds of formulas 3 and 4 of FIG. 1.

In addition, the modified porphyrins (referred to as "green porphyrin" or "Gp" herein) of the invention can be conjugated to specific ligands reactive with a target, such as receptor-specific ligands or immunoglobulins or immunospecific portions of immunoglobulins, permitting them to be more concentrated in a desired target tissue or substances. This conjugation permits further lowering of the required dose levels since the material is not wasted in distribution into other tissues whose destruction, far from being desired, must be avoided.

Thus, in one aspect, the invention relates to methods of locating or effecting cytotoxicity with respect to target materials using the hydro-monobenzoporphyrins of the invention either alone or as conjugates. The hydro-monobenzoporphyrins are green porphyrins (Gp) as shown in FIG. 1, and are localized specifically in vivo to certain target tissues, where their presence can be detected by fluorescence, or by other means when the Gp is provided with additional or alternate labeling. As indicated above, the specificity of the Gp can be further enhanced by conjugation to ligands specific for the target. In addition, when the Gp is irradiated in situ using light in the range of 670-780 nm, photoactivation results in cytotoxicity to the surrounding tissue. Cells to which the Gp is normally attracted include tumor cells, and neoplastic cells in general, as well as bacteria and other diseased tissues. The method can be applied either in vitro or in vivo, and, when applied in vivo, can be topical or systemic.

In another aspect, the invention relates to certain specific Gp compounds including those of formulas 3 and 4 designated herein "BPD", that are partially hydrolyzed forms containing free (non-esterified) carboxylic acid moieties or their salts in the $R^3$ substituents.

In other aspects, the invention relates to conjugates of the formulas Re*-L-Gp and Ig-L-Gp wherein Re* represents a ligand which is specific to, and capable of, binding a receptor at a cell surface, Ig represents an immunoglobulin or an immunologically reactive portion thereof, Gp represents a hydro-monobenzoporphyrin having an absorption maximum in the range of 670-780 nanometers, and L represents either a covalent bond linking these components or a linking moiety covalently linked to each of the Re* or Ig and Gp. The Gp is selected from a group of porphyrin derivatives obtained using Diels-Alder reactions of acetylene derivatives with protoporphyrin under conditions which effect a reaction at only one of the two available conjugated, nonaromatic diene structures present in the protoporphyrin-IX ring system (rings A and B). The formulas for Gp are shown in FIG. 1.

The invention is also directed to tripartite complexes which include Re*-L-Gp or Ig-L-Gp further conjugated to or associated with a label. The label may be bound either to the targeting component or to the Gp or both.

In another aspect, the invention relates to pharmaceutical compositions containing these active ingredients.

MODES CARRYING OUT THE INVENTION

The Hydro-monobenzoporphyrins (Gp)

Figure 3:
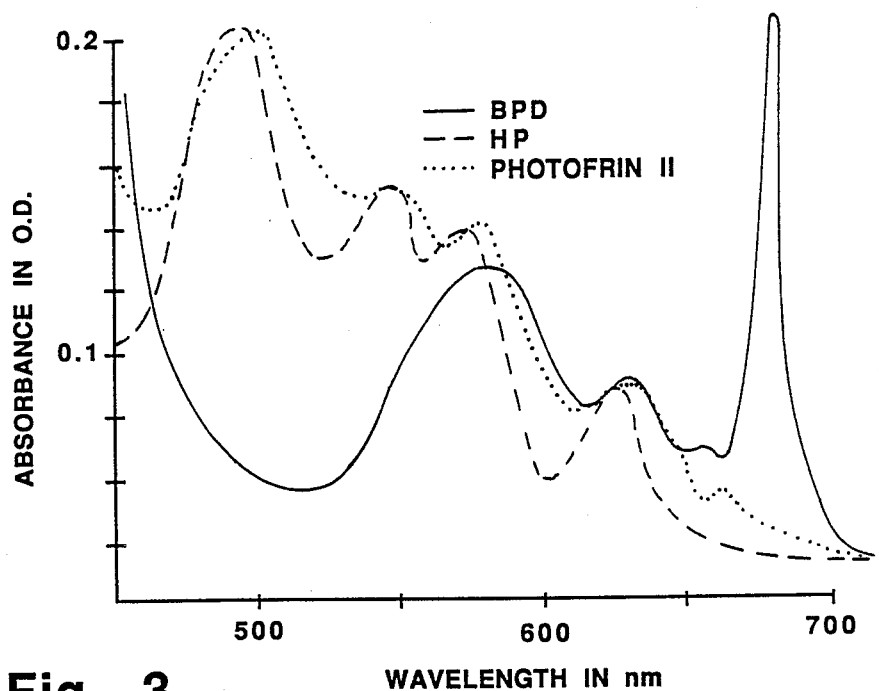
FIG. 3 shows a comparative absorption spectrum of BPD and prior art compositions.

All of the compositions of the invention employ as the light absorbing compound, a derivative of the protoporphyrin ring system which has a light absorption maximum in the range of 670-780 nanometers. FIG. 3 shows the absor-tion spectrum of BPD-DA wherein R is methyl in comparison to HPD and Photofrin® II compositions. Only BPD-DA has a major absorption peak at about 685 nm.

In general, this shift is achieved by effectively saturating one of the two $\pi$-bonds in one, but not two, of the four -yrrole rings which constitute the typical porphyrin system. In protoporphyrin-IX two of the pyrroles contain vinyl substitutions such that the exocyclic $\pi$-bond is conjugated to one of the two x-bonds in the ring. A Diels-Alder reaction involving one of these conjugated systems with an acetylene derivative dienophile results in a fused cyclohexadiene-referred to herein as "hydrobenzo"—fused to the A or B ring, and results in the desired shift in absorption maximum.

Specific preparation of some compounds useful in the invention or their precursors is described by Morgan, A.R., et al, *J Chem Soc Chem Commun* (1984) pp. 1047-1048; and by Pangka, B.S., et al, *J Organic Chem* (1986) 51:1094. As described in these publications, it had earlier been reported that protoporphyrin-IX dimethyl ester, when reacted with strong Diels-Alder dienophile reagents such as tetracyanoethylene, is derivatized to the hydro-dibenzo derivatives. However, it is clear that, as shown by these references, when acetylene is derivatized with more weakly electron withdrawing groups and used as a Diels-Alder reagent, hydro-monobenzo derivatives are formed. Thus, there are obtained directly from reaction of protoporphyrin with, for example dimethyl acetylene dicarboxylate (DMAD), compounds shown as formulas 1 and 2 of FIG. 1, wherein $R^1$ and $R^2$ represent the substituents on the original acetylene-derived Diels-Alder reagent, $R^1C \equiv CR^2$, in this case carbomethoxy. $R^1$ and $R^2$ are, generally, specifically carbalkoxy groups such as carbomethoxy or carboethoxy. $R^3$ represents substituents present on the porphyrin used in. he reaction or substituents derived therefrom. In the Morgan reference, the reaction substrate was protoporphyrin-IX dimethyl ester; thus the ligand $R^3$ was, in all cases, 2-carbomethoxyethyl.

The disclosed substituents in the Morgan and Pangka references for the acetylene-derived dienophile include phenylsulfonyl--i.e., SO$_2$Ph, either as a single substituent, as described in the foregoing references ($\beta$-phenylsulfonylpropiate) or, putatively, wherein both $R^1$ and $R^2$ are sulfonyl derivatives. In general, $R^1$ and $R^2$ are each, independently, moderately electron-withdrawing substituents, and are, most commonly, carbalkoxy, or alkyl or aryl sulfonyl, or any other activating substituents, which are not sufficiently electron-withdrawing to result in reaction with both A and B rings rather than reaction with only one. One of $R^1$ and $R^2$ may optionally be H while the other is an electron withdrawing substituent of sufficient strength to facilitate the Diels-Alder reaction.

As used herein, carboxy is, as conventionally defined, —COOH and carbalkoxy is —COOR, wherein R is alkyl. Alkyl is a saturated hydrocarbon of 1-6 carbon atoms such as methyl, n-hexyl, 2-methylpentyl, t-butyl, n-propyl, and so forth. Aryl or alkyl sulfonyl moieties have the formula $SO_2R$ wherein R is alkyl as above-defined, or is aryl, wherein aryl is phenyl optionally substituted with 1-3 substituents independently selected from halo (fluoro, chloro, bromo or iodo), lower alkyl (1-4C) or lower alkoxy (1-4C). In addition, one or both $R^1$ or $R^2$ can itself be aryl -i.e., phenyl optionally substituted as above-defined.

Figure 1:
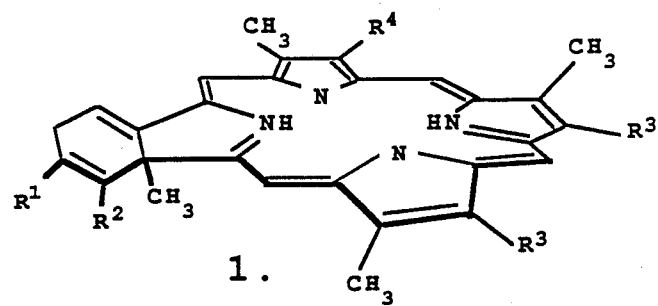
FIG. 1 shows the structures of green porphyrin compounds used in the method and conjugates of the invention.
Figure 1:
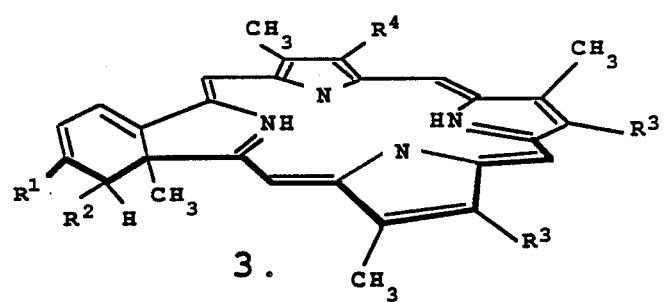
Figure 1:
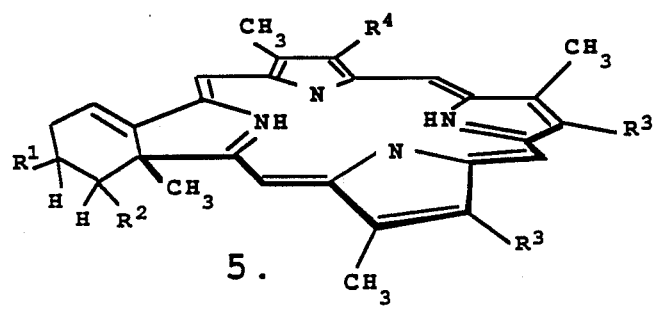

As shown in FIG. 1, the adduct formed by the reaction of $R^1$—C≡C—$R^2$ with the protoporphyrin-IX ring system ($R^3$ is a protected form of 2-carboxyethyl such as 2-carbomethoxy ethyl or 2-carboethoxy ethyl; $R^4$ is $CHCH_2$) are compounds of the formulas 1 and 2 wherein the compound in formula 1 results from addition to the A ring and formula 2 results from addition to the B ring. In these resulting products of formulas 1 and 2, $R^4$ remains $CHCH_2$, however this vinyl group is readily derivatized to other embodiments of $R^4$ by addition to or oxidation of the vinyl ring substituent of ring B in formula 1 or ring A in formula 2. The addition products can be further substituted if the added substituents are functional leaving groups—for example —Br may be substituted by —OH, —OR (R is alkyl 1-6 as above), or —$NH_2$, —NHR, —$NR_2$, etc. In preferred embodiments, one of the added substituents is hydrogen, and the other is selected from the group consisting of halo (fluoro, chloro, bromo or iodo), hydroxy, lower alkoxy, amino or an amide, sulfhydryl or an organo-sulfide or can be, itself, hydrogen. Addition to the vinyl group does not appreciably change the absorption spectrum of the resulting compound. The product of the Markovnikov addition of water provides a substituent structure analogous to the hematoporphyrin ring system at the relevant ring. Thus, the compounds of the invention include various groups as $R^4$ as will be further described below.

$R^3$ in protoporphyrin-IX is 2-carboxyethyl (—$CH_2CH_2COOH$). However, the nature of $R^3$ (unless it contains a π-bond conjugated to ring π-bond), is ordinarily not relevant to the progress of the Diels-Alder reaction or to the effectiveness and absorption spectrum of the resulting product. $R^3$ can thus be, for example, lower alkyl (1-4C), or ω-carboxyalkyl or carbalkoxy-alkyl (2-6C). The $R^3$ substituent may also be substituted with halogen as above-defined, or with other nonreactive substituents. However, as the convenient starting materials for the Gp compounds of the invention are the naturally occurring porphyrins, the preferred substituents for $R^3$ are $CH_2CH_2COOH$ or —$CH_2CH_2COOR$, wherein R is alkyl (1-6C).

It should be noted that while the nature of the $R^3$ substituent does not ordinarily influence the course of the Diels-Alder reaction by altering the nature of the diene substrate, derivatization may be necessary to promote the reaction by providing suitable solubility characteristics or to prevent interference with the reaction. Thus, the Diels-Alder reactions described by Morgan et al and by Pangka et al utilized the dimethylester of protoporphyrin-IX as a substrate in order to prevent interference with the reaction by the free carboxyl group and to provide suitable solubility characteristics.

In the Gp compounds of the invention, it has been found advantageous to hydrolyze or partially hydrolyze the esterified carboxy group in —$CH_2CH_2COOR$. The hydrolysis occurs at a much faster rate than that of the ester groups of $R^1$, $R^2$, and the solubility characteristics of the resulting compounds are more desirable than those of the unhydrolyzed form. Hydrolysis results in the diacid or monoacid products.

The hydro-monobenzoporphyrins which directly result from the Diels-Alder reaction described in the cited references can also be isomerized as therein described (see Morgan et al and Pangka et al (supra)) to compounds of formulas shown as 3 and 4 of FIG. 1 by treatment with suitable reagents such as triethylamine (TEA) in methylene chloride or 1,5-diaza bicyclo[5.4.0] undec-5-ene (DBU). The stereochemistry of the product is determined by the choice of reagent.

The depictions of compounds 3 and 4 in FIG. 1 do not show the relative position of the exocyclic methyl group (ring A of formula 3 and ring B of formula 4) with respect to the $R^2$ substituent. It has been found by these authors that rearrangement using TEA gives cis geometry for the angular methyl group and $R^2$, while treatment with DBU results in the trans product. The cis product is evidently kinetically controlled since treatment of the cis product with DBU results in a further rearrangement to trans stereochemistry. Thus, formulas 3 and 4 of FIG. 1 show the rearranged products generically, from either TEA or DBU catalyzed rearrangement in rings A and B respectively.

In addition, the Diels-Alder products can be selectively reduced by treating with hydrogen in the presence of palladium on charcoal to give the saturated ring analogs, shown as formulas 5 and 6 in FIG. 1, corresponding to the respective Diels-Alder products of rings A and B. These reduced products are less preferred embodiments, and are less useful in the method of the invention than the compounds of formulas 1-4.

The description set forth above with respect to the compounds of formulas 1 and 2 concerning derivatization by conversion of the remaining vinyl substituent ($R^4$) and with respect to variability of —$R^3$ applies as well to the compounds of formulas 3, 4, 5 and 6.

The compounds of formulas 3 and 4, and especially those which have hydrolyzed or partially hydrolyzed carbalkoxy groups in $R^3$, are most preferred. Compounds of the invention which contain —COOH may be prepared as the free acid or in the form of salts with organic or inorganic bases.

It will be noted that many of the compounds of FIG. 1 contain at least 1 chiral center and therefore exist as optical isomers. The conjugates and methods of the invention include compounds having both configurations of the chiral carbons, whether the compounds are supplied as isolates of a single stereoisomer or are mixtures of enantiomers and/or diasteriomers. Separation of mixtures of diasteriomers may be effected by any conventional means; mixtures of enantiomers may be separated by usual techniques of reacting them with optically active preparations and separating the resulting diasteriomers.

It should further be noted that the reaction products may be unseparated mixtures of A and B ring additions, e.g., mixtures of formulas 1 and 2 or 3 and 4 or 5 and 6. Either the separated forms—i.e., formula 3 alone or 4 alone, or mixtures in any ratio may be employed in the methods of therapy and diagnosis set forth herein.

The name "dihydro"-monobenzoporphyrin describes the direct and rearrangement products of the Diels-Alder reaction of the porphyrin ring system with $R^1C \equiv C—R^2$; "tetrahydro"-monobenzoporphyrin describes the foregoing reduced products of formulas 5 and 6, and "hexahydro"-monobenzoporphyrin describes the analogs containing the exocyclic "benzo" ring completely reduced. Hydro-monobenzoporphyrin is used generically to include all three classes of oxidation state. The monobenzoporphyrins per se are outside the scope of the invention as their absorption maxima do not fall within the required range.

Figure 2:
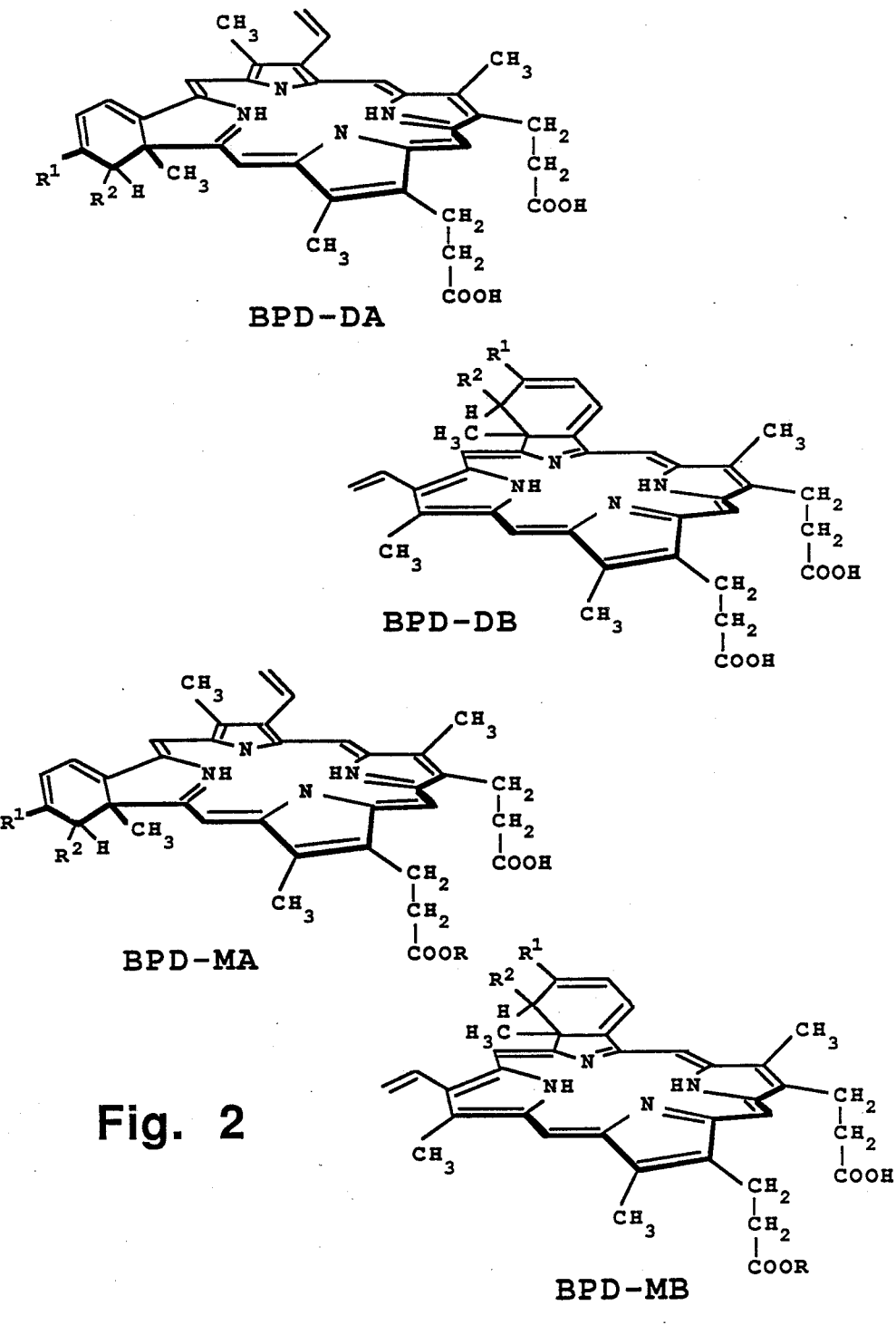
FIG. 2 shows the structures of four forms of hydromonobenzoporphyrin derivative (BPD).

FIG. 2 shows four particularly preferred compounds of the invention which have not been previously described in the art. These compounds are collectively designated benzoporphyrin derivative (BPD) as they are forms of Gp having the formula 3 or 4. These are hydrolyzed or partially hydrolyzed forms of the rearranged products of formula 3 and 4, wherein one or both of the protected carboxyl groups of $R^3$ are hydrolyzed. The ester groups at $R^1$ and $R^2$ hydrolyze relatively so slowly that conversion to the forms shown in FIG. 2 is easily effected.

For purposes of this description, $R^3$ is —CH$_2$COOR$^3$'. As shown in FIG. 2, each $R^{3'}$ is H in preferred compound BPD-DA, $R^1$ and $R^2$ are carbalkoxy, and derivatization is at ring A; BPD-DB is the corresponding compound wherein derivatization is at ring B. BPD-MA represents the partially hydrolyzed form of BPD-DA, and BPD-MB, the partially hydrolyzed form of BPD-DB. Thus, in these latter compounds, $R^1$ and $R^2$ are carbalkoxy, one $R^{3'}$ is H and the other $R^{3'}$ is alkyl (1-6C). The compounds of formulas BPD-MA and BPD-MB may be homogeneous wherein only the C ring carbalkoxyethyl or only the D ring carbalkoxyethyl is hydrolyzed, or may be mixtures of the C and D ring substituent hydrolyzates. In addition, mixtures of any two or more of BPD-MA, -MB, -DA and -DB may be employed in the methods of the invention.

As these hydrolyzed forms of the Diels-Alder product are previously undisclosed, the invention is also directed to these compounds. Thus, in another aspect, the invention is directed to compounds of the formulas shown in FIG. 2 wherein $R^1$ and $R^2$ are as above defined, and R is alkyl (1-6C). Preferred are embodiments wherein $R^1$ and $R^2$ are carbalkoxy, especially carbomethoxy or carboethoxy.

Certain other embodiments wherein $R^4$ is other than vinyl are also not disclosed in the art and the invention is directed to them, i.e., the invention is directed to the compounds shown in FIG. 1 wherein $R^1$ and $R^2$ are as above defined, each $R^3$ is independently —CH$_2$CH$_2$COOR$^{3'}$ wherein $R^{3'}$ is H or alkyl (1-6C), and $R^4$ is CHCH$_2$, CHOR$^{4'}$, COOR$^{4'}$,CH(OR$^{4'}$)CH$_3$, CH(OR$^{4'}$)CH$_2$OR$^{4'}$, —CH(SR$^{4'}$)CH$_3$, —CH(NR$^{4'}$)CH$_3$, —CH(CN)CH$_3$, —CH(COOR$_4$')CH$_3$, —CH(OOCR$^{4'}$)CH$_3$, —CH(halo)CH$_3$, and —CH(halo)CH$_2$(halo), wherein $R_{4'}$ is H, alkyl (1-6C), or an organic group of <12C derivatizable as shown, and wherein when $R^4$ is CHCH$_2$, both $R^3$ cannot be 2-carbalkoxy ethyl.

Compounds of the formulas 3 and 4 and mixtures thereof are particularly preferred. Also preferred are those wherein $R^1$ and $R^2$ are the same and are carbalkoxy, especially carbomethoxy or carboethoxy; also preferred are those wherein $R^4$ is —CHCH$_2$, CH(OH)CH$_3$ or —CH(halo)CH$_3$.

The compounds of formulas shown in FIG. 1 include those wherein $R^4$ is formed by addition to the vinyl groups of initial protoporphyrin products, Thus, $R^4$ can be any substitutent consistent with a facile addition reaction. Thus, both added substituents can be, for example, OH or halo, and these substituents can be further substituted.

The vinyl group can also be oxidized to obtain $R^4$ as CH$_2$OH, —CHO or COOCH and its salts and esters.

Thus, in general, $R^4$ represents any substituent to which the vinyl group —CH≡CH$_2$ is readily converted by oxidation or addition. Typical $R^4$ substituents includes:

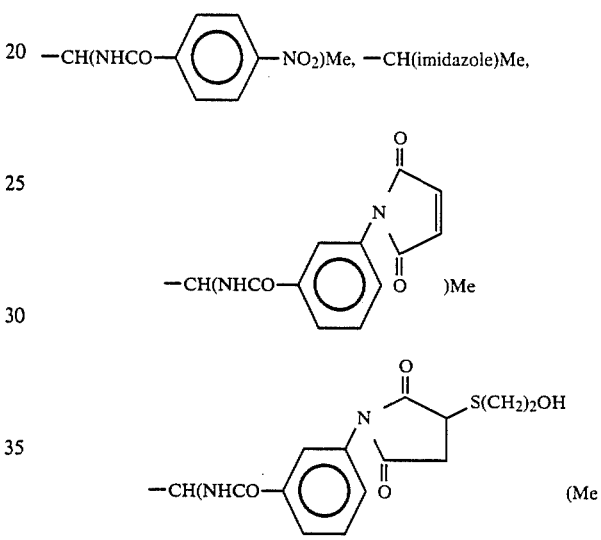

CH(OH)Me, —CHBrMe, —CH(OMe)Me, —CH(pyridinium bromide) Me, —CH(SH)Me and the disulfide thereof, —CHOHCH$_2$OH, and —CHO.

The Tarqet-Specific Component

The target-specific component can be, for example, an immunoglobulin or portion thereof or a ligand specific for receptor.

The immunoglobulin component can be any of a variety of materials. It may be derived from polyclonal or monoclonal antibody preparations and may contain whole antibodies or immunologically reactive fragments of these antibodies such as F(ab')$_2$, Fab, or Fab' fragments. Use of such immunologically reactive fragments as substitutes for whole antibodies is well known in the art. See, for example, Spiegelberg, H.L., in "Immunoassays in the Clinical Laboratory" (1978) 3:1-23.

Polyclonal anti-sera are prepared in conventional ways by injecting a suitable mammal with antigen to which antibody is desired, assaying the antibody level in serum against the antigen, and preparing anti-sera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, H.L, supra.

Particularly useful antibodies exemplified herein include the monoclonal antibody preparation CAMAL1 which can be prepared as described by Malcolm, A., et al, *Ex Hematol* (1984) 12:539–547; polyclonal or monoclonal preparations of anti-M1 antibody as described by Mew, D., et al, *J Immunol* (1983) 130:1473–1477 (supra) and B16G antibody which is prepared as described by Maier, T., et al, *J Immunol* (1983) 131:1843; Steele, J.K., et al, *Cell Immunol* (1984) 90:303.

The foregoing list is exemplary and certainly not limiting; once the target tissue is known, antibody specific for this tissue may be prepared by conventional means. Therefore the invention is applicable to effecting toxicity against any desired target.

The ligand specific for receptor, Re*, refers to a moiety which binds a receptor at cell surfaces, and thus contains contours and charge patterns which are complementary to those of the receptor. The ligand specific for receptor is symbolized in the formulas of the compounds of the invention as Re*, wherein the asterisk indicates that the moiety bound in the compound of the invention is not the receptor itself, but a substance complementary to it. It is well understood that a wide variety of cell types have specific receptors designed to bind hormones, growth factors, or neurotransmitters. However, while these embodiments of ligands specific for receptor are known and understood, the phrase "ligand specific for receptor", as used herein, refers to any substance, natural or synthetic, which binds specifically to a receptor.

Examples of such ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmitters, such as acetylcholine, serotonin, and dopamine. Any analog of these substances which succeeds in binding to the receptor is also included.

Linkage

The conjugation of the target-cell-specific component to the hydro-monobenzoporphyrin can be effected by any convenient means. For proteins, such as Ig and certain Re*, a direct covalent bond between these moieties may be effected, for example, using a dehydrating agent such as a carbodiimide, in which case L represents a covalent bond. A particularly preferred method of covalently binding hydro-monobenzoporphyrins to the immunoglobulin moiety is treatment with 1-ethyl-3-(3-dimethylamino propyl) carbodiimide (EDCI) in the presence of a reaction medium consisting essentially of dimethyl sulfoxide (DMSO). A preparation using this preferred procedure is illustrated in Example 3 below.

Of course, other dehydrating agents such as dicyclohexylcarbodiimide or diethylcarbodiimide could also be used as well as conventional aqueous and partially aqueous media.

Nonprotein receptor ligands can be conjugated to the Gp according to their relevant functional groups by means known in the art.

The active moieties of the conjugate may also be conjugated through linker compounds which are bifunctional, and are capable of covalently binding each of the two active components. A large variety of these linkers is commercially available, and a typical list would include those found, for example, in the catalog of the Pierce Chemical Co. These linkers are either homo or heterobifunctional moieties and include functionalities capable of forming disulfides, amides, hydrazones, and a wide variety of other linkages.

Other linkers include polymers such as polyamines, polyethers, polyamine alcohols, derivatized to the components by means of ketones, acids, aldehydes, isocyanates, or a variety of other groups.

The techniques employed in conjugating the active moieties of the conjugate include any standard means and the method for conjugation does not form part of the invention. Therefore, any effective technique known in the art to produce such conjugates falls within the scope of the invention, and the linker moiety is accordingly broadly defined only as being either a covalent bond or any linker moiety available in the art or derivable therefrom using standard techniques.

Label

For use in the method of the invention either the green porphyrin compounds per se or the conjugates may be further derivatized to a compound or ion which labels the drug. A wide variety of labeling moieties can be used, including radioisotopes, chromophores, and fluorescent labels. Radioisotope labeling is preferred, as it can be readily detected in vivo.

The compounds which are Gp alone or are conjugates of Gp with a specific binding substance can be labeled with radioisotopes by coordination of a suitable radioactive cation in the porphyrin system. Useful cations include technetium, gallium, and indium. In the conjugates, either or both the specific binding substances can be linked to or associated with label, or the label can be conjugated or coordinated with the Gp moiety itself.

Administration and Use

The improved photosensitizing compounds of the invention are thus useful in general, in the manner known in the art for hematoporphyrin derivative and for DHE. These materials are useful in sensitizing neoplastic cells or other abnormal tissue to destruction by irradiation using visible light—upon photoactivation, the compounds have no direct effect, nor are they entered into any biological event; however the energy of photoactivation is believed to be transferred to endogenous oxygen to convert it to singlet oxygen. This singlet oxygen is thought to be responsible for the cytotoxic effect. In addition, the photoactivated forms of porphyrin fluorescence which fluoresce can aid in localizing the tumor. Thus, the Gp compounds of the invention are not consumed or altered in exerting their biological effects.

Typical indications, known in the art, include destruction of tumor tissue in solid tumors, dissolution of plaques in blood vessels (see, e.g., U.S. Pat. No. 4,512,762); treatment of topical conditions such as acne, athletes foot, warts, papilloma, and psoriasis and treatment of biological products (such as blood for transfusion) for infectious agents, since the presence of a membrane in such agents promotes the accumulation of the drug.

The conjugates of the invention, or the hydromonobenzoporphyrins when employed alone are formulated into pharmaceutical compositions for administration to the subject or applied to an in vitro target using techniques known in the art generally. A summary of such pharmaceutical compositions may be found, for example, in *Remington's Pharmaceutical Sciences,* Mack Publishing Co., Easton, Pa., latest edition.

The conjugates and hydro-monobenzoporphyrins of the present invention, labeled or unlabeled, can be administered systemically, in particular by injection, or can be used topically. The Gp or conjugates can be used singly or as components of mixtures.

Injection may be intravenous, subcutaneous, intramuscular, or, even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in *Remington's Pharmaceutical Sciences* (supra).

If the treatment is to be localized, such as for the treatment of superficial tumors or skin disorders, the active conjugates or hydro-monobenzoporphyrins may be topically administered using standard topical compositions involving lotions, suspensions, or pastes.

The quantity of conjugate or green porphyrin derivative to be administered depends on the choice of active ingredient, the condition to be treated, the mode of administration, the individual subject, and the judgment of the practitioner. Depending on the specificity of the preparation, smaller or larger doses may be needed. For compositions which are highly specific to target tissue, such as those which comprise conjugates of the green porphyrin with a highly specific monoclonal immunoglobulin preparation or specific receptor ligand, dosages in the range of 0.05–1 mg/kg are suggested. For compositions which are less specific to the target tissue, larger doses, up to 1–10 mg/kg may be needed. The foregoing ranges are merely suggestive, as the number of variables in regard to an individual treatment regime is large and considerable excursions from these recommended values are expected.

EXAMPLES

The following examples are intended to illustrate the invention but not to limit its scope.

EXAMPLE 1

In Vitro Photosensitization by Green Porphyrins

Target cells were washed three times in serum-free medium (DME), counted and made up to a concentration of $10^7$ cells per ml.

For the "affinity" assay, in the dark, 100 μl of the target cell suspension and 100 μl of the test or control compound were mixed. "Labeling" was allowed to continue for one hour at 4° C., and labeled cells were washed in the dark three times with 3 ml medium each time and resuspended in fresh medium. The resuspended cells were then subjected to light exposure at 300–750 nanometers for 30 minutes.

In a "direct" assay the target cells were irradiated immediately upon addition of the test or control compound.

The effect of irradiation was estimated using methods appropriate to the target cells.

When human erythrocytes (RBCs) were used as target cells, the hemolysis caused by irradiation of control (hematoporphyrin, Hp) labeled and green porphyrin (Gp) labeled cells were estimated visually. The Gp used in this Example was the BPD-DB of FIG. 2 wherein $R^1$ and $R^2$ are carboethoxy. Repeated tests showed this green porphyrin to be 20–30 times more active than Hp in this assay. Thus, a concentration of 250 ng/ml Hp was required under the above conditions to obtain 50% hemolysis while only 10 ng/ml of green porphyrin was required to hemolyze 50% of the RBCs.

When the murine mastocytoma cell line P815 was used, the results were determined as follows:

The cells were labeled as above using concentrations of 10–50 ng/ml of Hp as control and the BPD-DB as the test substance. The resuspended cells were treated with 300–750 nm light for 30 minutes and the viability resulting was estimated by direct counting using eosin-Y exclusion, a standard procedure for differentiating living from dead cells.

In other determinations conducted as above, the cells recovered from light exposure were assayed for viability by incubating them for 18 hours in 10 μCi/ml tritium-labeled thymidine according to the standard procedure whereby thymidine incorporation is equated with viability. The cells were harvested and radioactivity uptake was measured by a scintillation counter.

Fifty percent of the P815 cells were killed at 580 ng/ml Hp, but at only 32 ng/ml green porphyrin (BPD-DB).

The results of each determination on a variety of cells is shown in Table 1 ($LD_{50}$ is the concentration of compound required to kill 50% of the cell population).

TABLE 1

| | $LD_{50}$ (ng/ml) | | | |
| | Direct test | | Affinity test | |
| Cell line | Gp | Hp | Gp | Hp |
|---|---|---|---|---|
| Normal lymphocytes | 4.2 | 31 | 11 | 100 |
| HL-60 | 3.5 | 64 | 7.2 | 145 |
| K562 | 70 | 770 | 33 | 2,500 |
| KG-1 | 163 | 960 | 80 | 2,350 |
| P815 | 32 | 580 | 26 | 1,300 |

EXAMPLE 2

Selective Binding of Green Porphyrin

P815 cells were incubated as described in Example 1 using 1–200 ng/ml Hp or Gp. The Gp was BPD-DB of FIG. 2 wherein $R^1$ and $R^2$ are carboethoxy. The cells were labeled in the dark for 30 minutes, washed free of unadsorbed porphyrins, resuspended, and then exposed to 300–750 nm light for another 30 minutes. Viability of the cells was established by tritiated thymidine incorporation after labeling with 20 μCi/ml tritiated thymidine and incubating at 37° C. for 18 hours.

The results showed that 50% of the p815 cells were destroyed at 6–20 ng/ml BPD-DB or at 200 ng/ml hematoporphyrin.

EXAMPLE 3

Preparation of Immunoconjugates

This example describes methods of preparation for immunoconjugates of four different antibody preparations with either hematoporphyrin (Hp) or green porphyrin (Gp); in this example, GP is BPD-DB of FIG. 2 wherein $R^1$ and $R^2$ are carboethoxy. The antibodies employed were CAMAL-1, anti-M1 antibody, and B16G antibody, all prepared as described hereinabove, and affinity purified rabbit/anti-mouse Ig (RαMIg). In addition, a purified irrelevant monoclonal preparation (C-MAb) was used where a control was desired.

One preparation of the conjugates is basically as described in Mew, D., et al, *J Immunol* (1983) 130:1473 (supra). Briefly, to 220 mg Hp.0.2 HCl (Sigma Chemical Co., St. Louis, MO) in 25 ml water and 0.8 ml N,N-dimethylformamide was added 20 mg 1-ethyl-3-(3-dimethylaminopropyl)-carbodiimide HCl (EDCI) in 0.6 ml water. After 30 minutes, this solution was mixed with 15 mg of the antibody protein dissolved in 5 ml distilled water and incubated for 5 hours. During this period, the pH of the solution was monitored and adjusted to between 6 and 7. Then 50 μl of monoethanolamine were added, and the solution was allowed to stand overnight at room temperature. The solution was dialyzed against 0.001M phosphate buffer pH 7.4 for four days with three changes per day and overnight against PBS. The conjugate of green porphyrin is analogously prepared.

In a preferred method, the conjugation is conducted in an entirely nonaqueous solvent.

In a typical protocol, 2 ml of a dispersion in DMSO containing 5 mg each of the Hp or Gp and the dehydrating agent is prepared and stirred for 30 minutes at room temperature under nitrogen. To this is added a dispersion containing 2 mg of the appropriate immunoglobulin in 2 ml of DMSO, and the resulting mixture stirred for another 10 minutes. This mixture is then worked up by dilution in phosphate-buffered saline, pH 7.4 (PBS) by adding 5 times the volume of PBS containing 50 μl monoethanolamine, and is then dialyzed against PBS using three changes of wash.

Alternatively, 2 ml of a dispersion containing 5 mg each of Hp or Gp, a linking agent, and a dehydrating agent is prepared and stirred for approximately 15 minutes at room temperature under nitrogen. To this is then added a dispersion containing about 2 mg of the immunospecific protein in 2 ml of tetrahydrofuran and the resulting mixture stirred for another 10 minutes. The mixture is then worked up as described above.

The foregoing procedures are appropriate for CAMAL-1 and for the remaining antibody preparations above listed.

In addition, the following preparations were made specifically with B16G and RαMIg:

B16G 11 mg of hematoporphyrin plus 11 mg EDCI in 4 ml spectral grade DMSO was stirred for 30 minutes under nitrogen at room temperature before the addition of 20 mg lyophilized B16G antibodies, prepared as described by Maier, T., et al, *J Immunol* (1983) 131:1843, in 2 ml DMSO. The resulting mixture was stirred for 40 seconds at room temperature and worked up as described above. The resulting product contained 375 μg Hp/mg B16G. A similar procedure is used substituting Gp for Hp.

RαMIg

400 μg of EDCI and 400 μg hematoporphyrin in 1 ml DMSO were stirred for 30 minutes under nitrogen at room temperature as above before the addition of 800 μg lyophilized RαMIg antibodies, prepared as described by Mew, D., et al, *J Immunol* (1983) 1473-1477, in 1 ml DMSO. The resulting mixture was stirred for 30 seconds and worked up as described above to obtain a product containing 200 μg Hp/mg RαMIg. A similar procedure is used substituting Gp for Hp.

EXAMPLE 4

Specificity of Immunoconjugates in Vitro

In the following determinations, the levels of antibody conjugation were as follows, expressed as μg Hp or green porphyrin (Gp) per mg immunoglobulin:

RαMIg-Hp: 110 μg/mg;
B16G-Hp, 156 μg/mg;
CAMAL-1-Hp, 260 μg/mg;
Anti-M1-Hp, 170 μg/mg;
C-MAb-Hp, 95 μg/mg;
RαMIg-Gp, 120 μg/mg;
B16G-Gp, 165 μg/mg
CAMAL-1-Gp, 75 μg/mg;
C-MAb-Gp 90 μg/mg.

The Ig-Hp and Ig-Gp conjugates are tested against cells in vitro by mixing the conjugates with the appropriate cell types, along with suitable controls, and then exposing the labeled cells to irradiation. Procedures for carrying out this assay were described in detail in Mew, D., et al, *Cancer Research* (1985) for CAMAL-1, and by Mew, D., et al, *J Immunol* (1983) for Anti-M1, both references cited hereinabove and incorporated herein by reference.

Briefly, for CAMAL-1, three cell lines, WC4, WC6 and WC2 (WC4 and WC6 produces the CAMAL antigen, but WC2 does not), are labeled with the appropriate Ig-Hp or Ig-Gp preparation as described above in Example 1. The labeled cell preparations containing $10^6$ cells each are introduced to Rose chambers and exposed to light activation with a laser at 630 nm. The results for various preparations are then compiled.

For the anti-M1 conjugate, M1 tumor cells are used as target cells and treated with the Ig-Hp, Ig-Gp conjugates or drug or antibody alone or the combination of antibody and drug, but uncoupled, by incubating them in 6% $CO_2$ humidified incubator at 37° for two hours. The cells are washed three times in PBS and then plated and exposed to fluorescent light overnight. The cells are assessed for viability by tritiated thymidine uptake as above.

For the B16G conjugates, A10, P815, and L1210 cells are used as target cells. (A10 cells are a T-cell hybridoma which secretes a B16G-reactive T suppressor factor; P815 cells are also reactive with B16G.) The in vitro study is done using a direct method employing the B16G-Hp or B16G-Gp conjugate or indirectly using unlabeled B16G antibodies and labeled RαMIg-Hp or RαMIg-Gp.

In a direct method, $5 \times 10^5$ cells are suspended in 1 ml DME/Hepes containing the appropriate Ig-drug conjugate as test or control at Hp or Gp concentrations of 320, 160, 80, 40 and 20 ng drug/ml. The cells are incubated in the dark at 37° for one hour, then washed three times in 5 ml DME/Hepes and then resuspended in 1 ml of the same buffer. Three 100 μl test portions of the labeled preparations are dispensed into flat bottom microtiter wells and the remainder of the cell suspensions (700 μl) are exposed to incandescent light (22.5 mW/cm$^2$) at a distance of 20 cm for one hour. Then three additional 100 μl aliquots are removed to microtiter wells. Tritium-labeled thymidine diluted in DME/-Hepes containing 20% FCS is then added to all microtiter wells in 100 μl aliquots so that 2 μCi of labeled thymidine is added to each well. Cultures are incubated for 18 hours at 37° C. and humidified 10% $CO_2$ and then harvested on a MASH harvester. Thymidine incorporation was measured with an Hp scintillation counter (Tri-Carb Model 4550). The results of this study for Ig-Hp are shown in Table 2.

TABLE 2

| B16G Hp | % killing of cell lines | | |
|---|---|---|---|
| (ng Hp/ml) | A10 | P815 | L1210 |
| 320 | 100 | 70 | 55 |
| 160 | 100 | 50 | 10 |
| 80 | 100 | 20 | 0 |
| 40 | 65 | 10 | 0 |
| 20 | 20 | 0 | 0 |
| C-MAb-Hp | | | |
| (ng Hp/ml) | A10 | P815 | L1210 |
| 320 | 63 | 75 | 50 |
| 160 | 35 | 48 | 15 |
| 80 | 0 | 25 | 0 |
| 40 | 0 | 12 | 0 |
| 20 | 0 | 0 | 0 |

In an indirect assay, the A10 suspended cells, prepared as described above, are exposed to 50 μg/ml of either B16G or a control antibody C-MAb at 4° C. for 30 minutes, washed in DME/Hepes, and then exposed for an additional 30 minutes at 4° C. in the dark to varying concentrations of RαMIg-Hp or RαMIg-Gp between 2 μg/ml and 15 ng/ml of Hp or Gp. The cells are assessed for viability using labeled thymidine uptake as described above. These results for Ig-Hp are shown in Table 3.

TABLE 3

| RαMIg-Hp | Primary antibody | |
|---|---|---|
| (ng/ml) | B16G | C-MAb |
| 500 | 100 | 30 |
| 250 | 85 | 22 |
| 125 | 75 | 5 |
| 52.5 | 60 | 2 |
| 31.2 | 47 | 3 |
| 15.6 | 18 | 1.5 |

Similar results are obtained using corresponding conjugates with Gp.

EXAMPLE 5

In Vivo Cytotoxicity of the Immunoconjugates

The efficacy of the conjugates and of the Gp compounds of the invention in vivo is also assessed. For the CAMAL-1 and anti-M1 conjugates, the procedures are as described in the two Mew, et al, papers referenced above in Example 4. The Gp compound alone shows superior results at appropriate wavelengths as compared to the Hp labeled conjugates.

For the B16G-Hp or B16G-Gp conjugates and for the Gp (BPD-DB) alone, the in vivo studies are conducted as follows:

The in vivo test relies on the indirect effect of a population of T-suppressor cells on tumors, which then serve as means to assess the effectiveness of the irradiation treatment. P815 mastocytoma cells grown in syngeneic DBA/2 mice stimulate T-suppressor cells specific for the tumor. These T-suppressor cells impede the development of specific T-killer cells which would otherwise aid in the regression of the tumor. The T-cell hybridoma designated A10 above secretes a T-suppressor factor which is associated with these T-suppressor cells. Thus, selective killing of these T-suppressor cell populations through reaction with conjugates in which the Ig is an antibody specific for the T-suppressor factor on the surface of the cells (namely B16G) should result in tumor regression in mice bearing the P815 tumors.

Therefore, in this assay, DBA/2 mice are injected in the right flank subcutaneously with 10$^4$ P815 cells to incorporate the tumor. On day eight, when the tumors are palpable (approx. 25–42 sq mm) the mice are randomly sorted into groups of eight and injected IV with 150 μl PBS containing nothing, Hp or Gp, B16G-Hp or B16G-Gp, B16G plus either drug, B16G alone or C-MAbHp or C-MAb-Gp. The levels of Hp are 50 μg per animal in all cases and B16G 310 μg in all cases (where appropriate).

The animals are maintained in the dark for two hours and then exposed to strong light at 300–750 nm and 22.5 mW/cm$^2$. The animals were then treated normally and monitored on a daily basis.

Animals treated with B16G Hp survived and were tumor free after 100 days. Results obtained are shown in Table 4.

TABLE 4

| Experiment | Treatment | Mean survival time (days) | No. of cures | % tumor-free after 100 days |
|---|---|---|---|---|
| 1 | PBS | 25.0 | 0/7 | 0 |
|   | B16G-Hp | 41.3 | 3/9 | 33 |
| 2 | PBS | 23.5 | 0/6 | 0 |
|   | Hp | 21.0 | 0/8 | 0 |
|   | B16G-Hp | 24.2 | 3/8 | 37.5 |
| 3 | PBS | 24.1 | 0/7 | 0 |
|   | Hp | 23.4 | 0/7 | 0 |
|   | B16G + Hp | 23.5 | 0/6 | 0 |
|   | B16G-Hp | 29.2 | 2/7 | 29 |
| 4 | PBS | 25.2 | 0/8 | 0 |
|   | B16G | 28.3 | 0/8 | 0 |
|   | Hp | 24.2 | 0/8 | 0 |
|   | B16G + Hp | 24.6 | 0/7 | 0 |
|   | B16G-Hp | 36.7 | 3/7 | 43 |
| 5 | PBS | 23.8 | 0/8 | 0 |
|   | Hp | 27.0 | 0/8 | 0 |
|   | C-MAb-Hp | 20.3 | 0/8 | 0 |
|   | B16G-Hp | 34.0 | 1/8 | 12.5 |

Similar results are obtained for Gp alone or Gp conjugates.

EXAMPLE 6

In Vitro Evaluation of BPD-DA, -MA, -DB and -MB

The four compounds shown in FIG. 2, wherein $R^1$ and $R^2$ are carbomethoxy, were tested in vitro as described in Example 1. All four compounds were photosensitive; the monoacid forms BPD-MA and BPD-MB were somewhat more active.

EXAMPLE 7

Biodistribution and Decradation

Biodistribution studies have been conducted using tritiated BPD-MA and BPD-MB. Table 5 shows the ratios between $^3$H-BPD-MA concentration in the tumor and in normal tissues determined at various times post-injection in mice bearing P815 tumor as the average for 3 mice.

TABLE 5

| Tissue | Time Post Injection | | | | | |
|---|---|---|---|---|---|---|
| | 3h | 24h | 48h | 72h | 96h | 168h |
| Blood | 0.52 | 1.45 | 1.37 | 1.66 | 2.77 | 3.65 |
| Brain | 3.76 | 3.06 | 2.92 | 2.69 | 4.18 | 6.91 |
| Heart | 1.09 | 1.71 | 1.63 | 1.46 | 2.24 | 2.51 |
| Intestine | 2.42 | 1.85 | 1.88 | 1.48 | 3.29 | 2.23 |
| Lung | 0.79 | 1.55 | 1.47 | 1.16 | 1.63 | 1.79 |
| Muscle | 2.68 | 2.98 | 2.77 | 2.16 | 3.45 | 4.23 |
| Skin | 2.57 | 1.64 | 1.95 | 1.57 | 2.03 | 3.51 |
| Stomach | 1.57 | 1.89 | 2.08 | 2.04 | 2.23 | 2.98 |

Tumor skin ratios are most favorable 3 hours after IV administration of the drug.

To determine biodegradability, tritiated BPD-MA was injected IV into P815 tumor-bearing mice. The mice were sacrificed at either 3 or 24 hours following injection and tumors, livers and kidneys were removed. The BPD-MA in these tissues was extracted and photoactivity was assessed in P815 target cells as described above in Example 1 under standard in vitro conditions. While 100% of BPD-MA in tumor was active at 3 hours, only 39% was active at 24 hours; both the liver and kidney degraded BPD more rapidly than did tumor tissue. Administration of tritiated BPD-MB in the same system gave similar results.

Similar studies using BPD-MA conjugated to an anti-keratin Mab in a model murine system carrying the KLN squamous tumor cell line showed improved concentration of the drug in the target tissue.

EXAMPLE 8

In Vivo Photosensitization by BPD

Studies of potential photosensitizers were performed using the M-1 rhabdomyoscercoma system in DBA/J2 mice. The compositions to be tested were diluted to a concentration of 800 µg/ml in PBS from a stock solution in DMSO at 8 mg/ml (except Photofrin® II, which was diluted directly from the clinical vial). Animals (8 per group) received 0.1 ml (80 µg) of material IV 24 h prior to exposure to light, provided by a 150 W tungsten bulb, red filter (transmits light >600 nm), hot mirror (reflects light >720 nm) and 2 fiber optics, at 567 Jo/cm$^2$.

The results, shown in Table 6, indicate all BPD compounds tested gave positive results. The superior results shown by Photofrin® II compositions are explainable by the observation that initial tumor sizes were smaller (a result of chance).

TABLE 6

| Photosensitizer | Days Tumor Free (PR) | Number of Cures* | Tumor Volume at Time of Light Treatment (mm$^3$) |
|---|---|---|---|
| None | 0.5 | 2 | 22.4 ± 7.8 |
| Photofrin ® II composition | 21.3 | 5 | 11.9 ± 6.9 |
| BPD-MA | 9.2 | 4 | 19.0 ± 13.0 |
| BPD-MB | 10.6 | 3 | 18.2 ± 11.0 |
| BPD-DA | 10.7 | 4 | 18.7 ± 9.9 |
| BPD-DB | 10.6 | 3 | 25.4 ± 16.4 |

*Animals whose tumors regressed and who remained tumor-free for 30 days.

Similar studies, except using a light dose of 378 To/cm$^3$ resulted in the outcome shown in Table 7.

TABLE 7

| Photosensitizer | Number of Animals | Days Tumor-free | Number of Cures |
|---|---|---|---|
| None | 11 | 0.1 | 2 |
| Photofrin II | 10 | 9.5 | 4 |
| BPD-MA | 10 | 13.2 | 4 |
| BPD-MB | 9 | 8.7 | 6 |
| BPD-DA | 15 | 2.5 | 4 |
| BPD-DB | 13 | 13.0 | 8 |

The foregoing results are preliminary, and the assay protocols have not yet been optimized.

EXAMPLE 9

Alternate In Vivo Assay

Mice bearing small tumors were injected IV with drug to be tested. Three hours later the animals were sacrificed and their tumors removed. The tumor cells were teased apart to form a single cell suspension, and the cells were plated at 10$^5$/ well and exposed to light at a prescribed dose. The plates were incubated overnight and assayed for viability by MTT assay.

The results of one study are shown in Table 7.

TABLE 8

| Photosensitizer | Dose (µg/mouse) | Light Dose (Jo) | % Kill |
|---|---|---|---|
| BPD-MA | 33 | 5.7 | 22.0 |
| | 40 | 3.8 | 32.5 |
| | 80 | 3.8 | 63.5 ± 2.1 |
| | 80 | 3.8 | 53.7 ± 6.2 |
| BPD-MB | 33 | 5.7 | 25.2 |
| BPD-DA | 80 | 3.8 | 11.0 |
| | 80 | 7.6 | 26.0 |

Thus, the BPD forms tested were active in this assay; it appears light intensity and drug levels are subject to optimization and correlation.

EXAMPLE 10

Comparison of BPD to Photofrin® II Compositions

Figure 4:
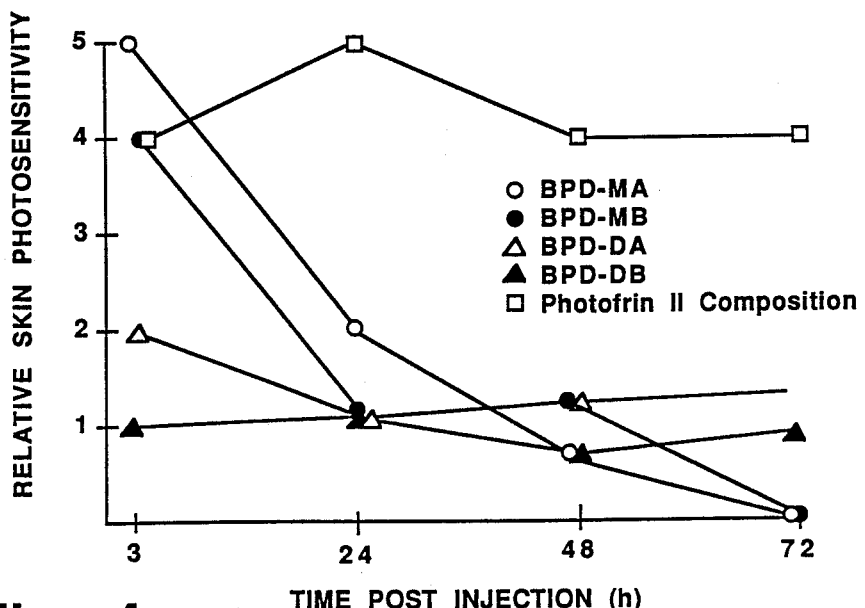
FIG. 4 shows the results of a skin sensitivity assay using BPD.

Mice bearing P815 tumors were shaved and injected with equivalent amounts of photosensitizer, and exposed to 72 Jo/cm$^2$ (80 mw/cm$^2$-15 min-full spectrum) at various time intervals. Skin biopsies were taken at 24 and 48 hours after light irradiation and visual evaluations were made blind. The results of these evaluations are shown in FIG. 4. BPD-MA and, to a lesser extent, BPD-MB had major photosensitizing activity, under these conditions; this was only present when light treatment was given 3 hours post drug administration, consistent with the biodegradability of these compounds.

EXAMPLE 11

Preparation of Compounds of the Invention

The following compounds have been prepared using the above-described Diels-Alder reaction of MeOO-C—C≡C-COOMe with the dimethyl ester of protophorphyrin IX, followed by rearrangement to the forms shown as formulas 3 and 4 of FIG. 1 and by subsequent treatment to hydrolyze or modify the propionic ester on rings C and D and/or to modify the unreacted vinyl group on the A or B ring remaining after the Diels-Alder reaction with the B or A ring, as the case may be. The products are compounds of the formula:

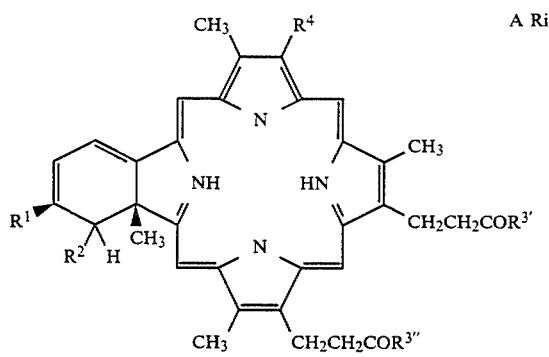
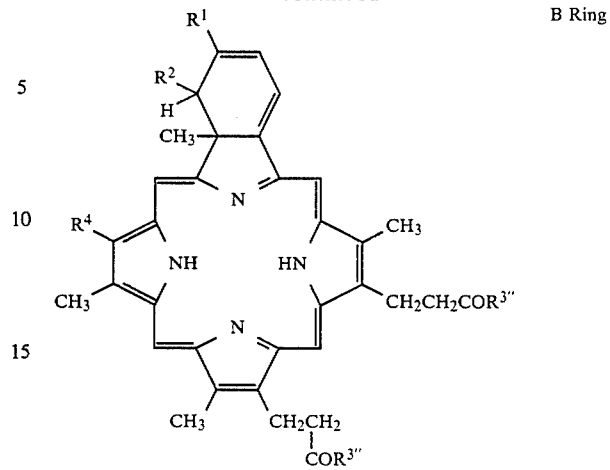

wherein R¹ and R² are, in all cases, COOMe.
The compounds prepared are as follows:

| | R³'' (C) | R³'' (D) | A-Ring R⁴ |
|---|---|---|---|
| 1. | OMe | OMe | CHCH$_2$ |
| 2. | OH | OMe | CHCH$_2$(BPD-MA) |
| 3. | OMe | OH | CHCH$_2$(BPD-MA) |
| 4. | OH | OH | CHCH$_2$(BPD-DA) |
| 5. | OMe | OMe | CH(NH$_2$)Me |
| 6. | OMe | OMe | CH(NHCO—⟨phenyl⟩—NO$_2$)Me |
| 7. | OH | OH | CH(NHCO—⟨phenyl⟩—NO$_2$)Me |

| | R³' (C) | R³' (D) | B-Ring R⁴ |
|---|---|---|---|
| 1. | OMe | OMe | CHCH$_2$ |
| 2. | OH | OMe | CHCH$_2$ |
| 3. | OMe | OH | CHCH$_2$ |
| 4. | OH | OH | CHCH$_2$ |
| 5. | OMe | OMe | CH(NH$_2$)Me |
| 6. | OH | OH | CH(NH$_2$)Me |
| 7. | OMe | OMe | CH(NH$_2$)(CH$_2$)$_6$NH$_2$ |
| 8. | OH | OH | CH(NH$_2$)(CH$_2$)$_6$NH$_2$ |
| 9. | OCD$_3$ | OCD$_3$ | CH(NH$_2$)(CH$_2$)$_6$NH$_2$ |
| 10. | OMe | OMe | CH(imidazolyl)CH$_3$ |
| 11. | OMe | OMe | CH(NHCO—⟨phenyl-maleimide⟩) |
| 12. | OMe | OMe | CH(NHCO—⟨phenyl-succinimide-S(CH$_2$)OH⟩) |

| | | |
|---|---|---|
| 13. | OMe OMe | CH(OH)Me |
| 14. | OMe OMe | CHBrMe |
| 15. | OMe OMe | CH(OMe)Me |
| 16. | OMe OMe | CH(pyridinium Br)Me |
| 17. | NH(CH$_2$)$_6$NH$_2$ | NH(CH$_2$)$_6$NH$_2$  CHCH$_2$ |
| 18. | R$^{3'}$—R$^{3'}$—NH(CH$_2$)$_6$NH— | CHCH$_2$ |
| 19. | OMe OMe | CH(SH)CH$_3$ |
| 20. | OMe OMe | disulfide |
| 21. | OMe OMe | CHO |
| 22. | OMe OMe | CHOHCH$_2$OH |

We claim:
1. A compound of the formula

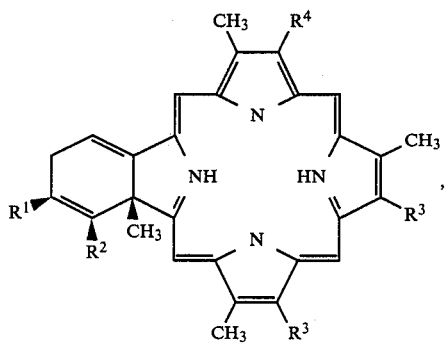

,

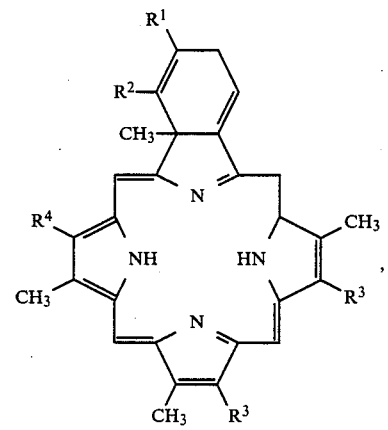

,

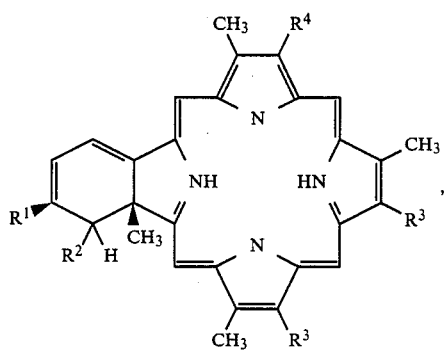

,

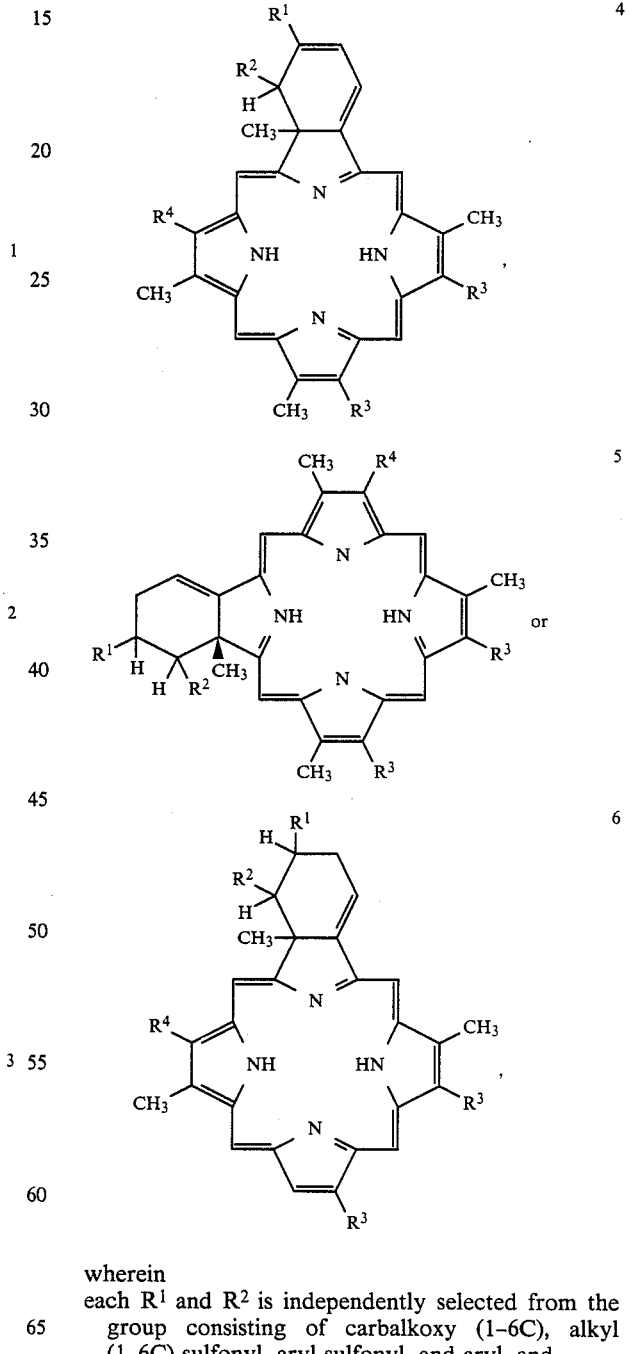

wherein
each $R^1$ and $R^2$ is independently selected from the group consisting of carbalkoxy (1–6C), alkyl (1–6C) sulfonyl, aryl sulfonyl, and aryl, and
each $R^3$ is independently CH$_2$CH$_2$COOR$^{3'}$ where $R^{3'}$ is H or alkyl (1–6C); and $R^4$ is CHCH$_2$, CH$_2$OR$^{4'}$, CH(OR$^{4'}$)CH$_3$, CH(OR$^{4'}$)CH$_2$OR$^{4'}$, —CH(SR$^{4'}$)CH$_3$, —CH(NR$^{4'}_2$)CH$_3$, —CH(CN)CH$_3$, —CH(COOR$^{4'}$)CH$_3$, —CH(OOCR$^{4'}$,)CH$_3$, —CH(halo)CH$_3$, and —CH(halo)CH$_2$(halo), wherein R$^{4'}$ is H, alkyl (1–6C), with the proviso that if $R^4$ is CHCH$_2$, both R$^{3'}$, cannot be alkyl.

2. The compound of claim 1 wherein $R^1$ and $R^2$ are carbalkoxy.

3. The compound of claim 2 wherein $R^1$ and $R^2$ are carbomethoxy or carboethoxy.

4. The compound of claim 2 which is of formulae 3 or 4 of FIG. 1.

5. The compound of claim 2 wherein $R^4$ is selected from —CHCH$_2$, —CH(OH)CH$_3$ and —CH(halo)CH$_3$.

6. The compound of claim 2 which is selected from compounds of the formula

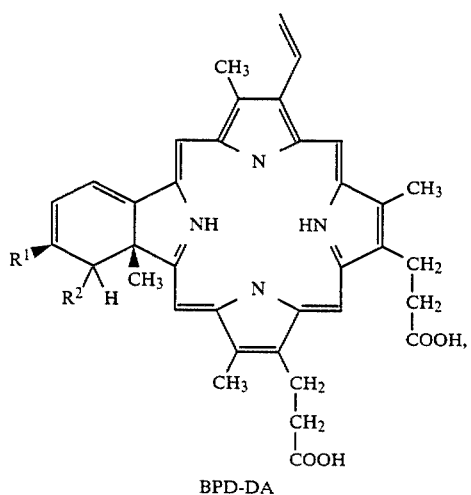

BPD-DA

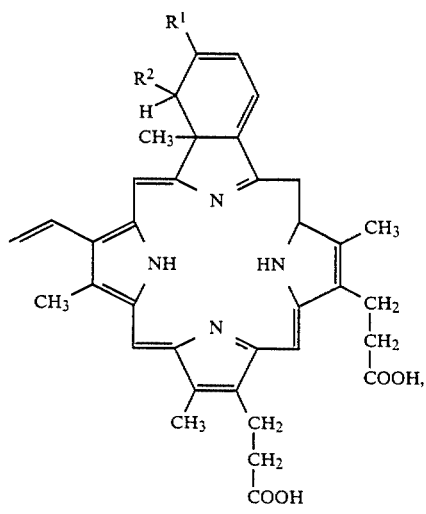

BPD-DB

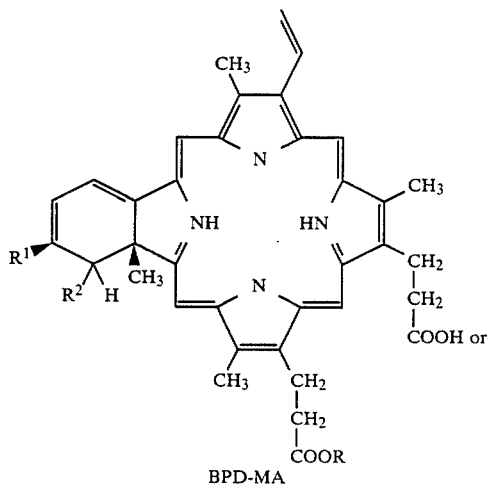

BPD-MA

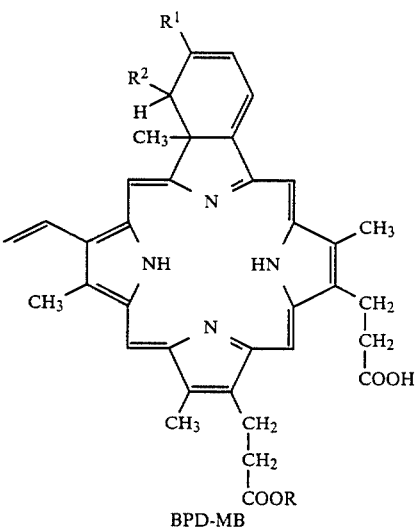

BPD-MB wherein R is alkyl (1–6C).

7. The compound of claim 5 which is of the formula

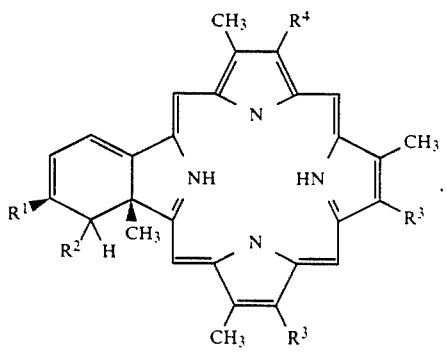

or

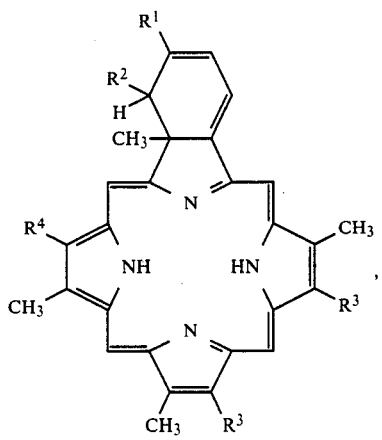

8. A pharmaceutical composition which is useful in targeting specific biological material which composition comprises an effective amount of the compound of claim 1 in admixture with at least one pharmaceutically acceptable excipient.

9. A pharmaceutical composition which is useful in targeting specific biological material which composition comprises an effective amount of the compound of claim 5 in admixture with at least one pharmaceutically acceptable excipient.

10. A pharmaceutical composition which is useful in targeting specific biological material which composition comprises an effective amount of the compound of claim 6 in admixture with at least one pharmaceutically acceptable excipient.

11. A pharmaceutical composition which is useful in targeting specific biological material which composition comprises an effective amount of the compound of claim 7 in admixture with at least one pharmaceutically acceptable excipient.

* * * * *

UNITED STATES PATENT AND TRADEMARK OFFICE
CERTIFICATE OF CORRECTION

PATENT NO. : 4,920,143  Page 1 of 6
APPLICATION NO. : 07/221161
DATED : April 24, 1990
INVENTOR(S) : Levy et al.

It is certified that error appears in the above-identified patent and that said Letters Patent is hereby corrected as shown below:

Replacement Formal Drawings for U.S. Patent No. 4,920,143

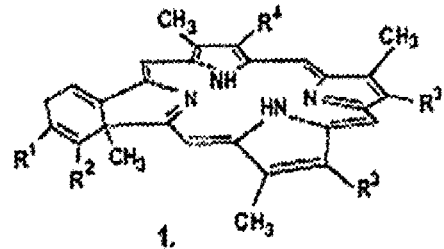

1.

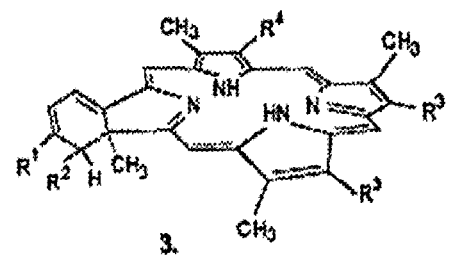

3.

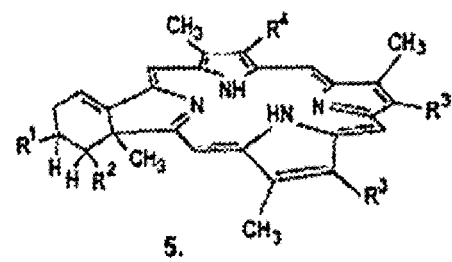

5.

FIG. 1

UNITED STATES PATENT AND TRADEMARK OFFICE
CERTIFICATE OF CORRECTION

PATENT NO. : 4,920,143  Page 2 of 6
APPLICATION NO. : 07/221161
DATED : April 24, 1990
INVENTOR(S) : Levy et al.

It is certified that error appears in the above-identified patent and that said Letters Patent is hereby corrected as shown below:

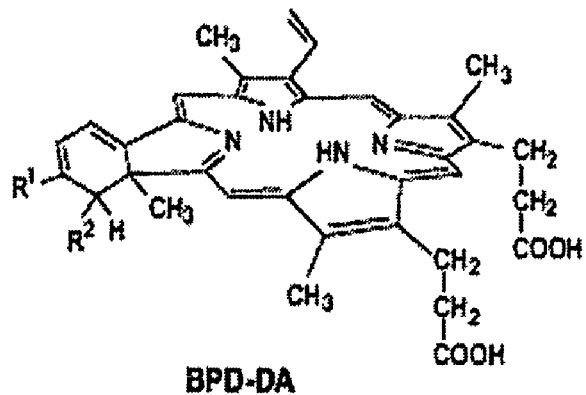

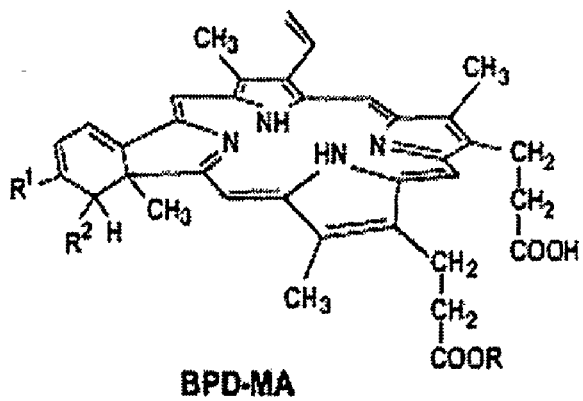

FIG. 2

UNITED STATES PATENT AND TRADEMARK OFFICE
CERTIFICATE OF CORRECTION

PATENT NO.        : 4,920,143                                        Page 3 of 6
APPLICATION NO.   : 07/221161
DATED             : April 24, 1990
INVENTOR(S)       : Levy et al.

It is certified that error appears in the above-identified patent and that said Letters Patent is hereby corrected as shown below:

Replacement Drawing, A Ring, Column 19, Lines 1-15

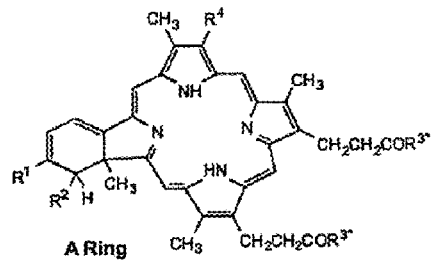

Replacement Drawing, B Ring, Column 20, Lines 1-19

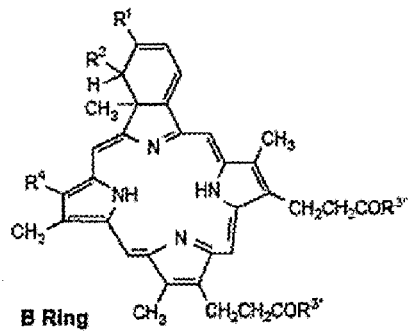

Replacement Drawing, Claim 1, Compound 1, Column 21, Lines 24-36

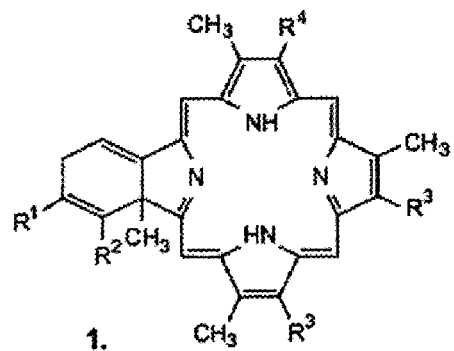

UNITED STATES PATENT AND TRADEMARK OFFICE
CERTIFICATE OF CORRECTION

PATENT NO.       : 4,920,143                              Page 4 of 6
APPLICATION NO.  : 07/221161
DATED            : April 24, 1990
INVENTOR(S)      : Levy et al.

It is certified that error appears in the above-identified patent and that said Letters Patent is hereby corrected as shown below:

Replacement Drawing, Claim 1, Compound 2, Column 21, Lines 39-54

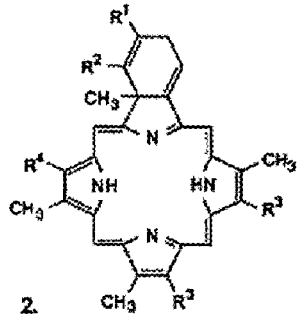

Replacement Drawing, Claim 1, Compound 3, Column 21, Lines 55-67

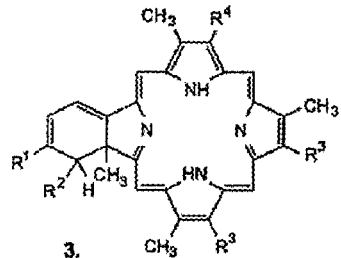

Replacement Drawing, Claim 1, Compound 5, Column 22, Lines 31-44

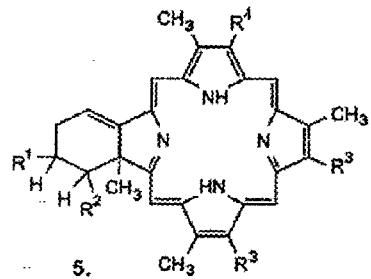

UNITED STATES PATENT AND TRADEMARK OFFICE
CERTIFICATE OF CORRECTION

PATENT NO. : 4,920,143
APPLICATION NO. : 07/221161
DATED : April 24, 1990
INVENTOR(S) : Levy et al.

Page 5 of 6

It is certified that error appears in the above-identified patent and that said Letters Patent is hereby corrected as shown below:

Replacement Drawing, Claim 1, Compound 6, Column 22, Lines 45-61

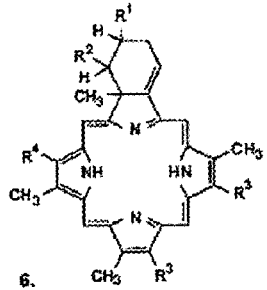

Replacement Drawing, Claim 6, Compound BPD-DA, Column 23, Lines 25-44

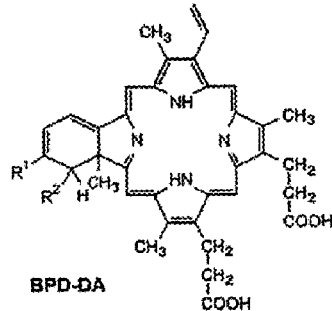

Replacement Drawing, Claim 6, Compound BPD-DB, Column 23, Lines 45-65

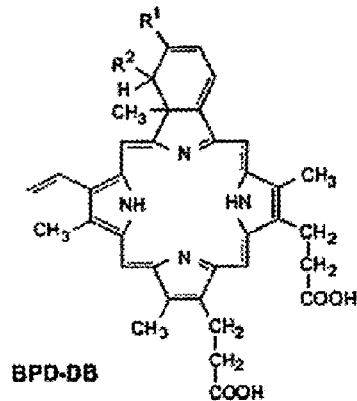

UNITED STATES PATENT AND TRADEMARK OFFICE
CERTIFICATE OF CORRECTION

PATENT NO. : 4,920,143
APPLICATION NO. : 07/221161
DATED : April 24, 1990
INVENTOR(S) : Levy et al.

It is certified that error appears in the above-identified patent and that said Letters Patent is hereby corrected as shown below:

Replacement Drawing, Claim 6, Compound BPD-MA, Column 24, Lines 3-20

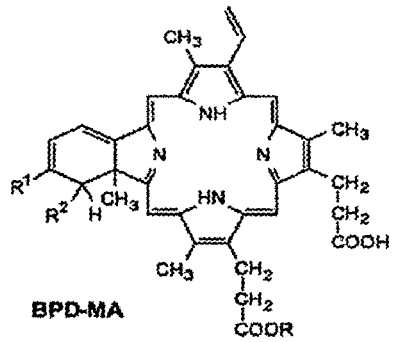

Replacement Drawing, Claim 7, Compound 3, Column 24, Lines 47-60

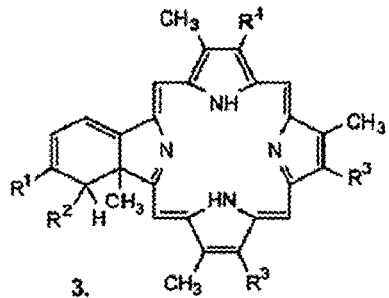

Signed and Sealed this

Twenty-fourth Day of October, 2006

JON W. DUDAS
*Director of the United States Patent and Trademark Office*